US012623057B2

(12) United States Patent (10) Patent No.: US 12,623,057 B2

Moulton et al. (45) Date of Patent: May 12, 2026

(54) SECUREMENT ASSEMBLY AND METHOD FOR CENTRAL VENOUS ACCESS DEVICES AND SURGICAL DRAINS

(71) Applicant: THE REGENTS OF THE UNIVESITY OF COLORADO, A BODY CORPORATE, Denver, CO (US)

(72) Inventors: Steven Moulton, Cherry HL VLG, CO (US); Christopher Seighman, Denver, CO (US); Joshua Eng-Morris, Boulder, CO (US); Bryan Norman, Boulder, CO (US); Gabriel Chapel, Littleton, CO (US); Tyler Mironuck, Lafayette, CO (US)

( * ) Notice: Subject to any disclaimer, the term of this patent is extended or adjusted under 35 U.S.C. 154(b) by 841 days.

(21) Appl. No.: 17/802,511

(22) PCT Filed: Feb. 26, 2021

(86) PCT No.: PCT/US2021/019984

§ 371 (c)(1),
(2) Date: Aug. 25, 2022

(87) PCT Pub. No.: WO2021/174054

PCT Pub. Date: Sep. 2, 2021

(65) Prior Publication Data

US 2023/0114722 A1 Apr. 13, 2023

Related U.S. Application Data

(60) Provisional application No. 62/982,481, filed on Feb. 27, 2020.

(51) Int. Cl.
*A61M 25/02* (2006.01)

(52) U.S. Cl.
CPC ....... *A61M 25/02* (2013.01); *A61M 2025/024* (2013.01); *A61M 2025/0246* (2013.01); *A61M 2025/0266* (2013.01)

(58) Field of Classification Search
CPC .... A61M 2025/0246; A61M 2025/024; A61M 2025/028; A61M 25/02
See application file for complete search history.

(56) References Cited

U.S. PATENT DOCUMENTS 4,517,971 A * 5/1985 Sorbonne .............. A61M 25/02
604/174
4,659,329 A * 4/1987 Annis ................... A61M 25/02
604/327

(Continued)

FOREIGN PATENT DOCUMENTS

EP 0931560 7/1999

OTHER PUBLICATIONS

ISA; International Search Report and Written Opinion dated Jun. 9, 2021 in PCT/US2021/019984.

*Primary Examiner* — Deanna K Hall
(74) *Attorney, Agent, or Firm* — Capital Patent & Trademark Law Firm, PLLC

(57) ABSTRACT

A securement assembly for supporting and stabilizing a vascular access device, such as a tunneled central venous access devices (CVAD) or a surgical drain, is provided herein. The securement assembly may comprise a base and a lid. The base may include a central post about/around which the external portion of the access device or surgical drain may be wrapped. The lid may extend from the base and may be configured to cover the external portion of the access device or surgical drain (when installed). In various embodiments, the base and the lid collectively define an annular chamber around the central post of the base.

20 Claims, 9 Drawing Sheets

(56)                 References Cited

U.S. PATENT DOCUMENTS

| | | | |
|---|---|---|---|
| 4,711,636 | A | 12/1987 | Bierman |
| 5,916,199 | A | 6/1999 | Miles |
| 6,387,076 | B1 | 5/2002 | Landuyt |
| 2008/0097491 | A1 | 4/2008 | Gobel |
| 2009/0306574 | A1* | 12/2009 | Kopperschmidt .. A61M 5/1418 604/6.16 |
| 2011/0060311 | A1 | 3/2011 | Barolat |

* cited by examiner

1

SECUREMENT ASSEMBLY AND METHOD FOR CENTRAL VENOUS ACCESS DEVICES AND SURGICAL DRAINS

CROSS-REFERENCE TO RELATED APPLICATIONS

This application is a national stage application of PCT/US2021/019984, filed on Feb. 26, 2021, entitled "SECUREMENT ASSEMBLY AND METHOD FOR TUNNELED CENTRAL VENOUS ACCESS DEVICES AND SURGICAL DRAINS", which claims priority to U.S. Provisional Patent Application Ser. No. 62/982,481, filed on Feb. 27, 2020, the entire contents of which are incorporated herein by reference in their entirety.

FIELD

The present disclosure relates to tunneled central venous access devices and/or surgical drains, and more particularly to a securement assembly for venous access devices and/or surgical drains.

BACKGROUND

Central venous access devices (CVADs) facilitate the delivery of fluids and medications to and/or from a patient. For example, CVADs may be used for the administration of parenteral nutrition, blood products, chemotherapeutics, a wide variety of medications, and other intravenous fluids to patients. Certain types of CVADs, such as an external tunneled CVADs, are 'tunneled' under the skin and into the bloodstream. They are commonly directed into a subclavian or jugular vein to the junction of the superior vena cava and right atrium of the heart, leaving an external port available for venous access. Pediatric patients, for example, may heavily rely on CVADs throughout a treatment process or their entire life. Unfortunately, conventional CVAD dressing and securement methods and assemblies have various shortcomings.

Conventional CVAD securement methods do not provide sufficient protection and/or retention for the CVAD. For example, current methods do not adequately protect patients from bloodstream infections, nor do they safeguard from inadvertent dislodgement, catheter thrombosis or occlusion, catheter fracture, or skin erosion at the exit site. Dislodgement may require removal and/or replacement of the CVAD. Further, conventional CVAD dressing and securement assemblies are generally uncomfortable, especially for younger patients with smaller torsos and more sensitive skin.

Although there are various methods for securing catheters, these conventional devices are used specifically for peripherally inserted central-line catheters (PICC) and do not work with external tunneled CVADs. In addition, these conventional solutions focus mainly on the exit site and redundant catheter; they do not address securement of the external port. Further, conventional solutions are often changed every few days (or more frequently if they become soiled), and nurses or other practitioners may frequently check the exit site to look for signs of infection or accidental dislodgement. Importantly, the external lines and/or external port of CVADs are often not properly secured, and thus are left dangling out of the patient where they may get caught on surrounding objects, thereby increasing the chances of dislodgement and/or increasing the discomfort for the patient.

The use of surgical drains is commonplace in many types of surgical procedures and every surgeon is familiar with Jackson-Pratt (JP) and Blake drains. These drains are used throughout the body in a wide variety of surgical procedures to evacuate fluid from a body cavity, or post-surgical fluid that may be produced by a wound. The portion of a Jackson-Pratt drain that is placed inside a body cavity or in a closed space wound is composed of a flat, rectangular silicone or Silastic drain with multiple perforations and internal ridges. The rectangular, internal portion is fused to a soft silicone or Silastic tube, which exists through the skin and is attached to a reservoir that provides intermittent or, more commonly, continuous suction. The design of the Blake drain is that of a cylindrical silicone or Silastic catheter with a solid crossed-shaped center and four open fluted channels to prevent plugging of or at the draining perforations. There is an even transition between the internal, perforated cylindrical portion to the nonperforated portion, which exits through a hole in the skin.

Jackson-Pratt and Blake drains are composed of a soft silicone, Silastic or similar material. They are designed to provide constant drainage and not collapse when under suction. They are sutured to the skin at the skin exit site, which is typically covered with a sterile, clear plastic adhesive dressing. The clear plastic dressing is usually changed every few days (or more frequently if soiled), and nurses or other practitioners may frequently check the exit site for signs of drainage and/or infection, or dislodgement of the drain. Similar to external tunneled CVADS, the external tubing of JP and Blake drains and their associated drainage reservoir may not be properly secured. They may be left dangling out of the patient where they can get caught on surrounding objects, thereby increasing the chances of dislodgement and/or increasing the discomfort for the patient.

SUMMARY

In various embodiments, the present disclosure provides a securement assembly for an access device ("access device") or surgical drain. The securement assembly may comprise a base and a lid. The base may include a central post about/around which an external portion of the access device may be wrapped. The lid may extend from the base and may be configured to cover the external portion of the access device (when installed). In various embodiments, the base and the lid collectively define an annular chamber around the central post of the base.

In various embodiments, at least one of the base and the lid comprises a rim that forms an outer sidewall of the annular chamber. In various embodiments, the rim defines one or more crenels that facilitate insertion of the external portion of the access device into the annular chamber. In various embodiments, the assembly further includes an adhesive layer coupled to the base. In various embodiments, the assembly further includes a clip extending from at least one of the base and the lid, wherein the clip is configured to detachably retain a port of the external portion of the access device or suction bulb of a surgical drain.

In various embodiments, the clip is a first clip, wherein the securement assembly further comprises a second clip extending from at least one of the base and the lid, wherein the second clip is also configured to detachably retain a port of the external portion of the access device. In various embodiments, the clip comprises a finger tab protruding from an upper surface of the clip. In various embodiments, the clip extends from the base and bends around more than 180 degrees such that a terminating end of the clip is facing back toward the lid. In various embodiments, the clip extends from the base and bends around about 235 degrees.

In various embodiments, the lid comprises a post receptacle configured to receive the central post of the base. The central post and the post receptacle may have a D-shaped cross-section (or other, non-circular cross-section to facilitate proper orientation between the two when connected together). In various embodiments, the central post comprises a protrusion and a recess is defined in a wall of the post receptacle, wherein the recess is configured to receive the protrusion to couple the lid to the base, to prevent the two components from being separated one from the other, which could be a choking hazard. In various embodiments, a radially inward surface of the wall of the post receptacle comprises a channel for receiving the protrusion during inserting of the central post into the post receptacle. In various embodiments, the protrusion comprises an upper surface that is slanted and a lower surface that is perpendicular to the central post.

The forgoing features and elements may be combined in various combinations without exclusivity, unless otherwise expressly indicated herein. These features and elements, as well as the operation of the disclosed embodiments, will become more apparent in light of the following description and accompanying drawings.

Figure 1A:
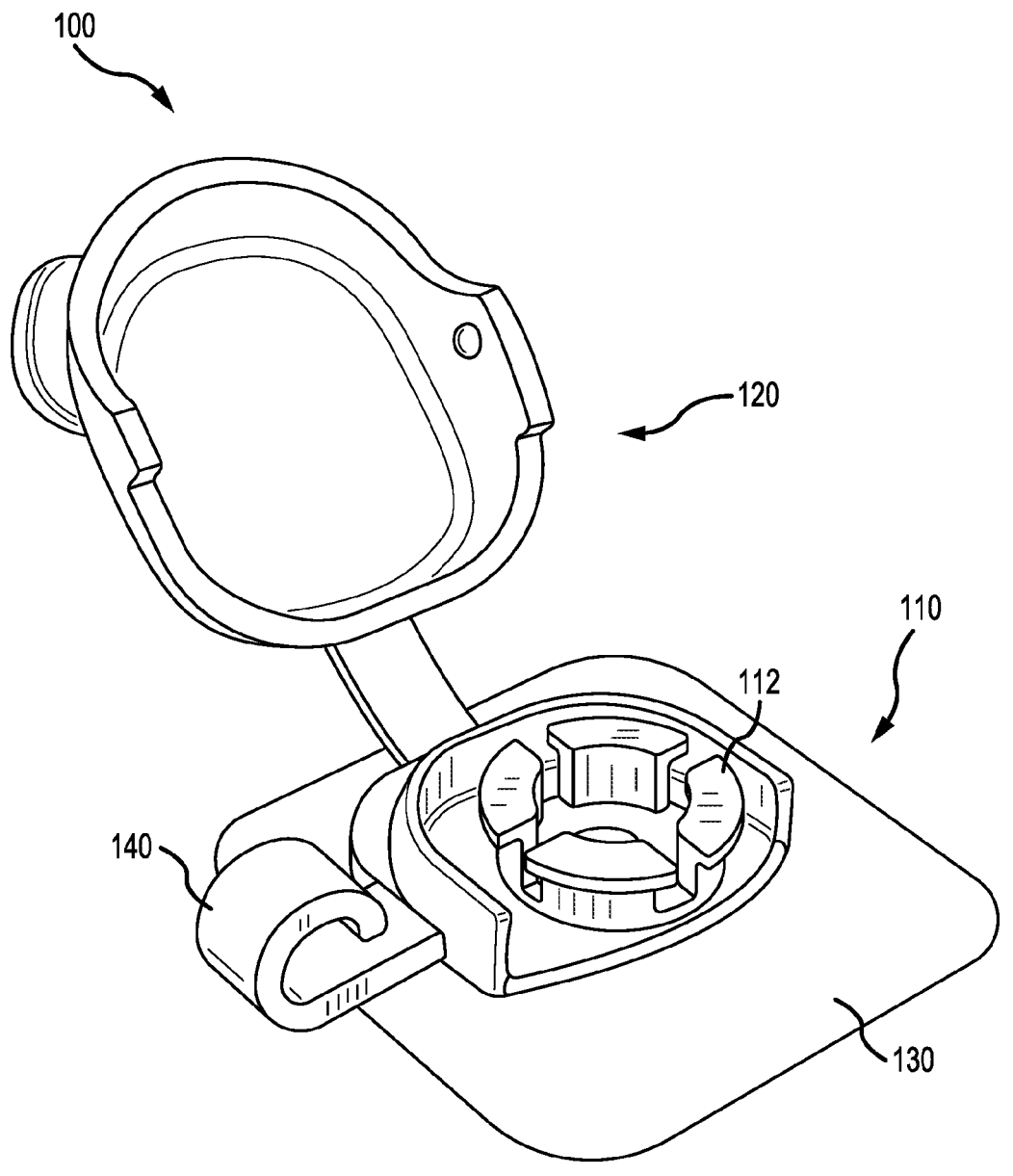
FIGS. 1A and 1B show various views of a securement assembly for securing the external portion of an access device (e.g., a catheter) or surgical drain, in accordance with various embodiments.

The subject matter of the present disclosure is particularly pointed out and distinctly claimed in the concluding portion of the specification. A more complete understanding of the present disclosure, however, may best be obtained by referring to the detailed description and claims when considered with the drawing figures.

DETAILED DESCRIPTION

The detailed description of exemplary embodiments herein refers to the accompanying drawings, which show exemplary embodiments by way of illustration. While these exemplary embodiments are described in sufficient detail to enable those skilled in the art to practice the disclosure, it should be understood that other embodiments may be realized and that logical changes and adaptations in design and construction may be made in accordance with this disclosure and the teachings herein without departing from the spirit and scope of the disclosure. Thus, the detailed description herein is presented for purposes of illustration only and not of limitation.

In accordance with example embodiments, the present disclosure provides a securement assembly for supporting and stabilizing a vascular access device, such as a tunneled central venous access devices (CVAD), or a surgical drain. An external tunneled CVAD is a device that is percutaneously inserted into a central vein of a patient and tunneled, subcutaneously, out of the body to facilitate the administration of fluids, medications, and other therapies. These vascular access devices (or simply "access devices") generally refer to catheters or other tubular structures used for interfacing with the vascular system of a patient, according to various embodiments. The securement assembly disclosed herein is generally configured to support, secure, retain, and/or protect the external portion (e.g., external lines and/or external ports) of vascular access devices, thereby inhibiting accidental dislodgement of the access device, minimizing infection risks, improving the patient's comfort, simplifying the management of the external portion of the access device, and/or otherwise addressing the aforementioned shortcomings of conventional methods and dressings, according to various embodiments. For example, and as described in greater detail below, the securement assembly may facilitate quick and easy securement/retention of the external portion of an access device and may be configured to prevent objects or articles from catching on the external portion of the access device.

It will be apparent to those skilled in the art that various modifications and variations can be made in the present disclosure without departing from the spirit or scope of the disclosure. For example, although many details and embodiments disclosed herein pertain to using the securement assembly for CVADs and surgical drains, the disclosure is not necessarily limited to these specific devices. That is, the details and embodiments of the securement assembly disclosed herein may be applied more generally for the securement of external portions of enteral, vesical, and/or other parenteral access devices. Thus, it is intended that the embodiments described herein cover the modifications and variations of this disclosure provided they come within the scope of the appended claims and their equivalents.

As used herein, the terms "upper," "above," "elevated," and/or "top" refer to components or surfaces that are facing away from or are disposed comparatively further away from the skin surface of the patient. Similarly, the terms "lower," "below," "under," and/or "bottom" refer to components or surfaces that are facing toward or are disposed comparatively closer to the skin surface of the patient. As used herein, the term "catheter" refers to a thin, flexible tube used to administer fluids, medications, and other therapies. The term "exit site" refers to an external location on a patient's body from which a catheter exits a subcutaneous tunnel. The term "occlusion dressing" refers to a substantially air and water-tight sheet-like dressing used for first aid and wound care. The term "PICC" refers to a peripherally inserted central venous catheter that is similar to a CVAD, but is percutaneously inserted a short distance into a peripheral vein instead of being tunneled under the skin to a central vein.

Figure 1B:
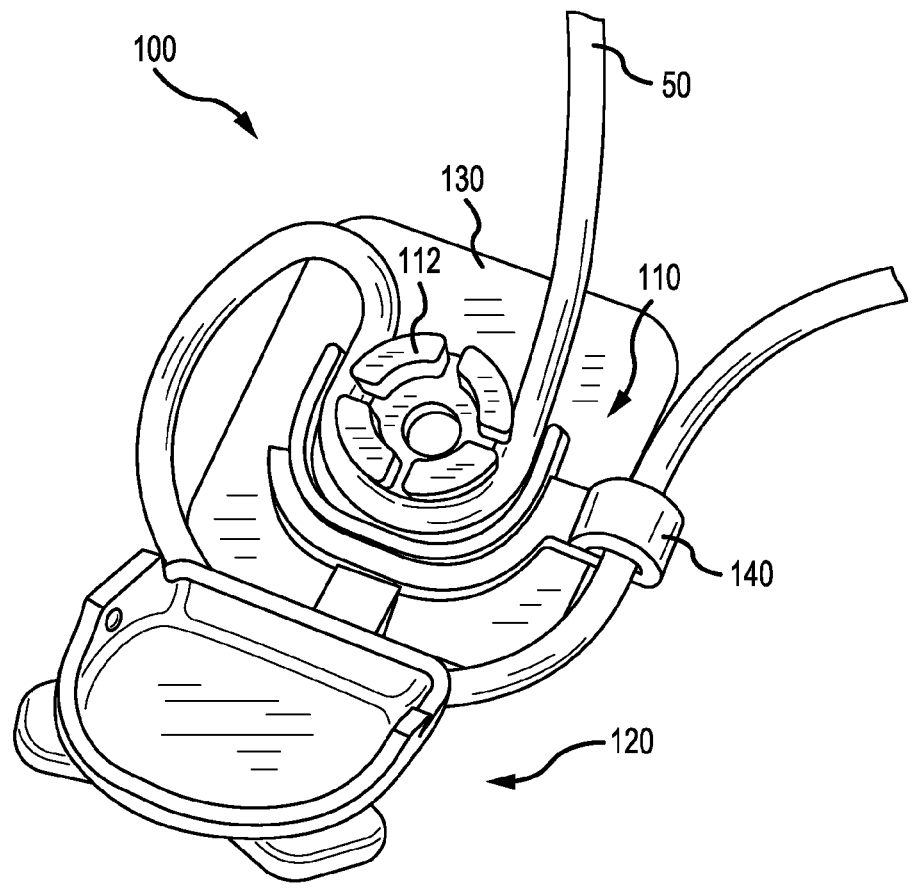
Figure 2A:
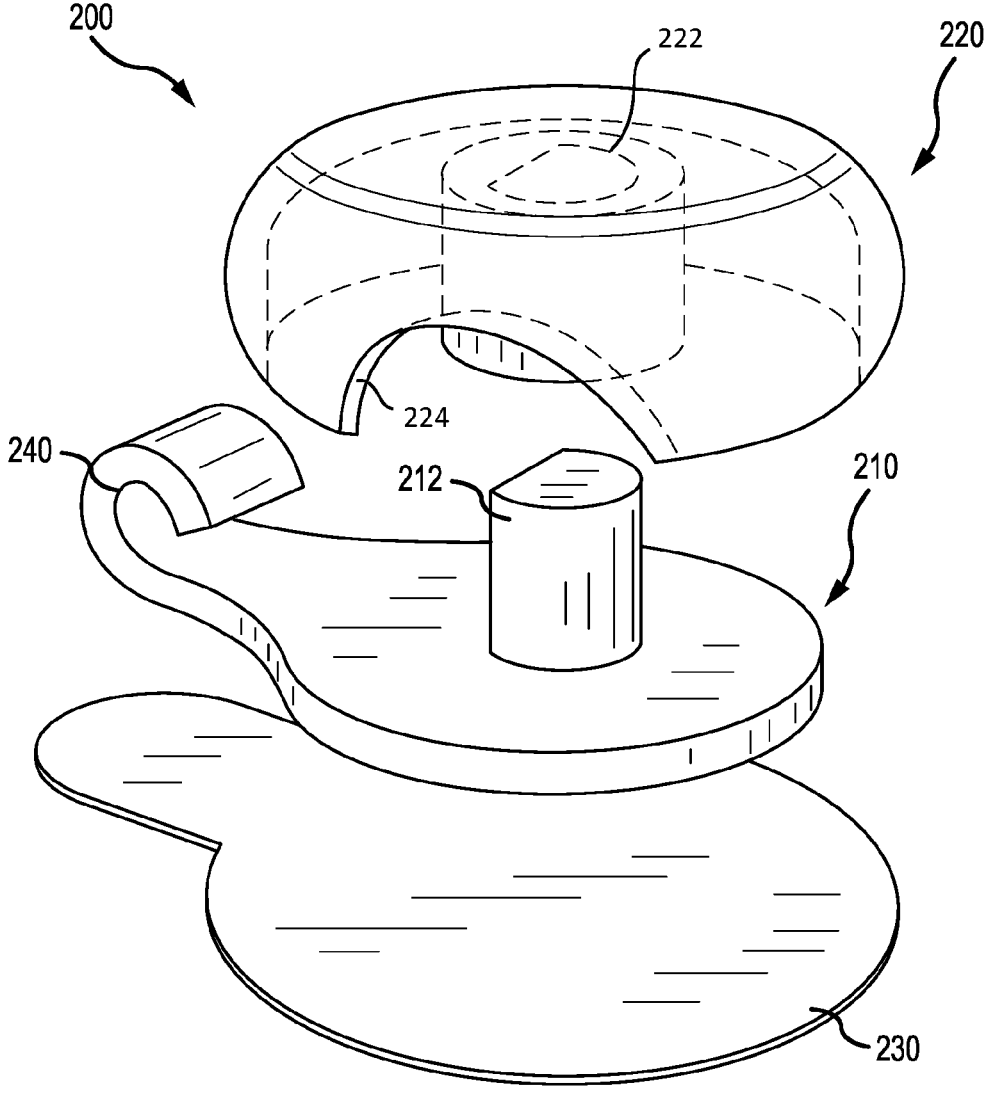
FIGS. 2A, 2B, and 2C show various views of another implementation of a securement assembly for securing the external portion of an access device or surgical drain, in accordance with various embodiments.
Figure 2B:
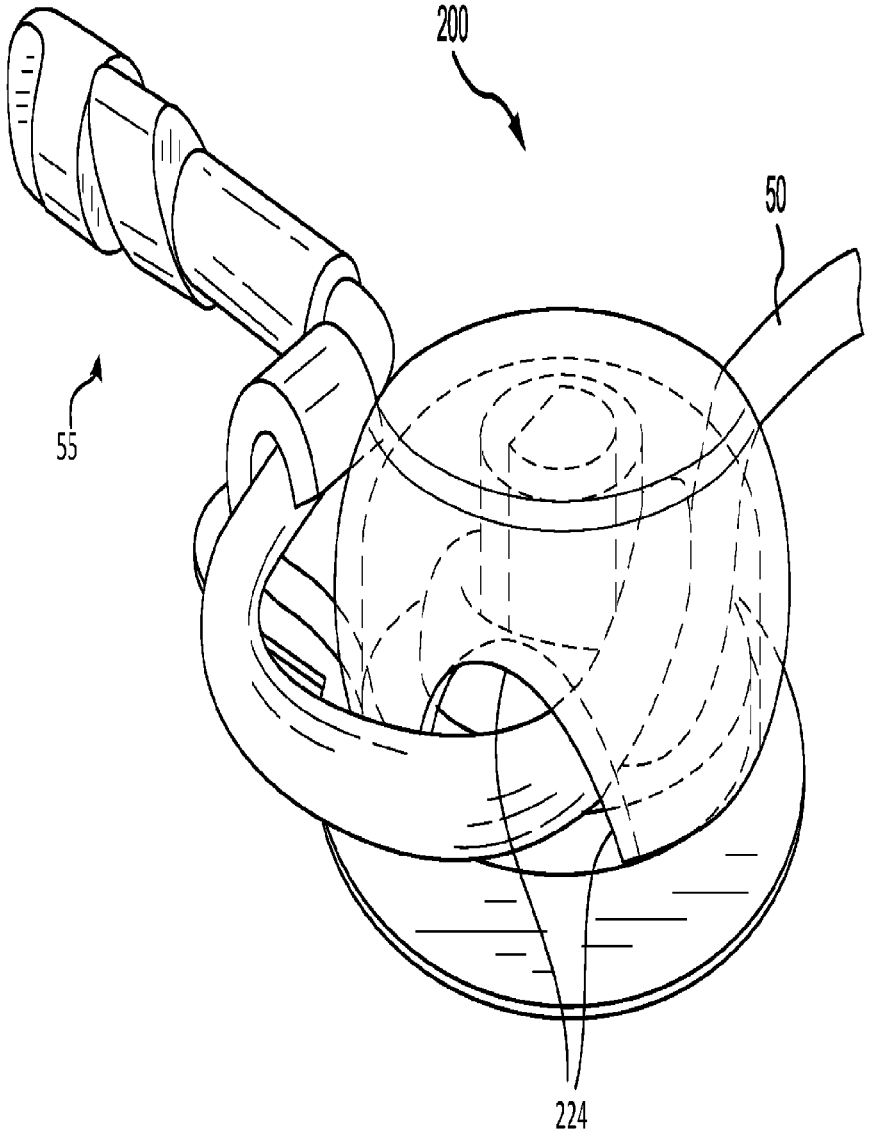
Figure 2C:
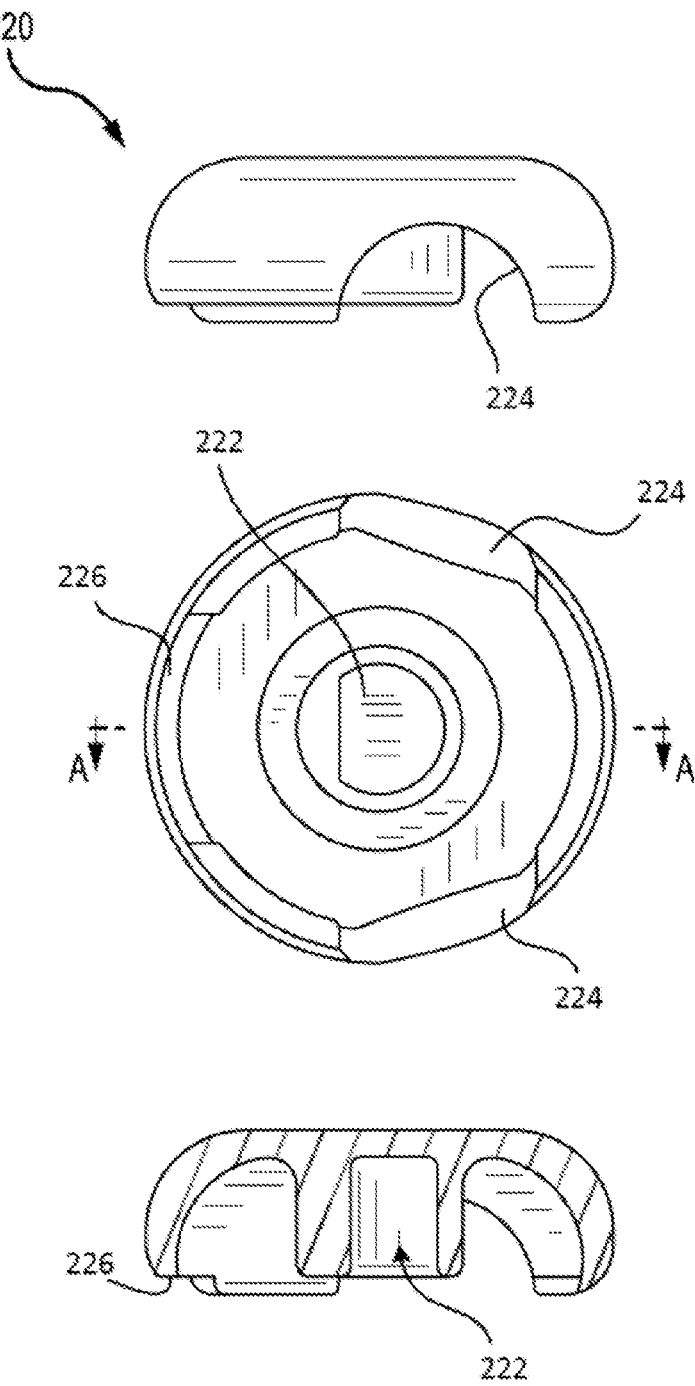
Figure 4:
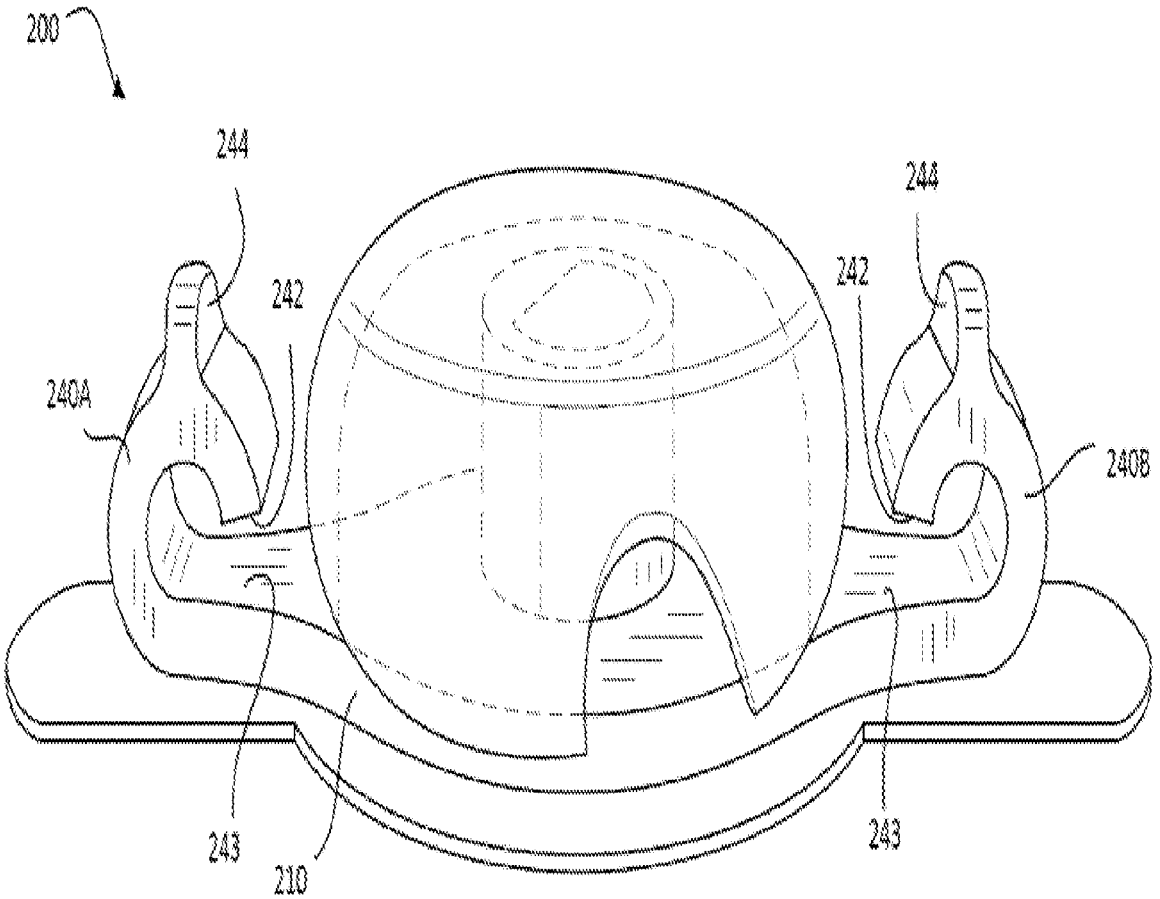
FIG. 4 shows a view of a securement assembly having two clips for securing the external portion of an access device or surgical drain, in accordance with various embodiments.
Figure 5A:
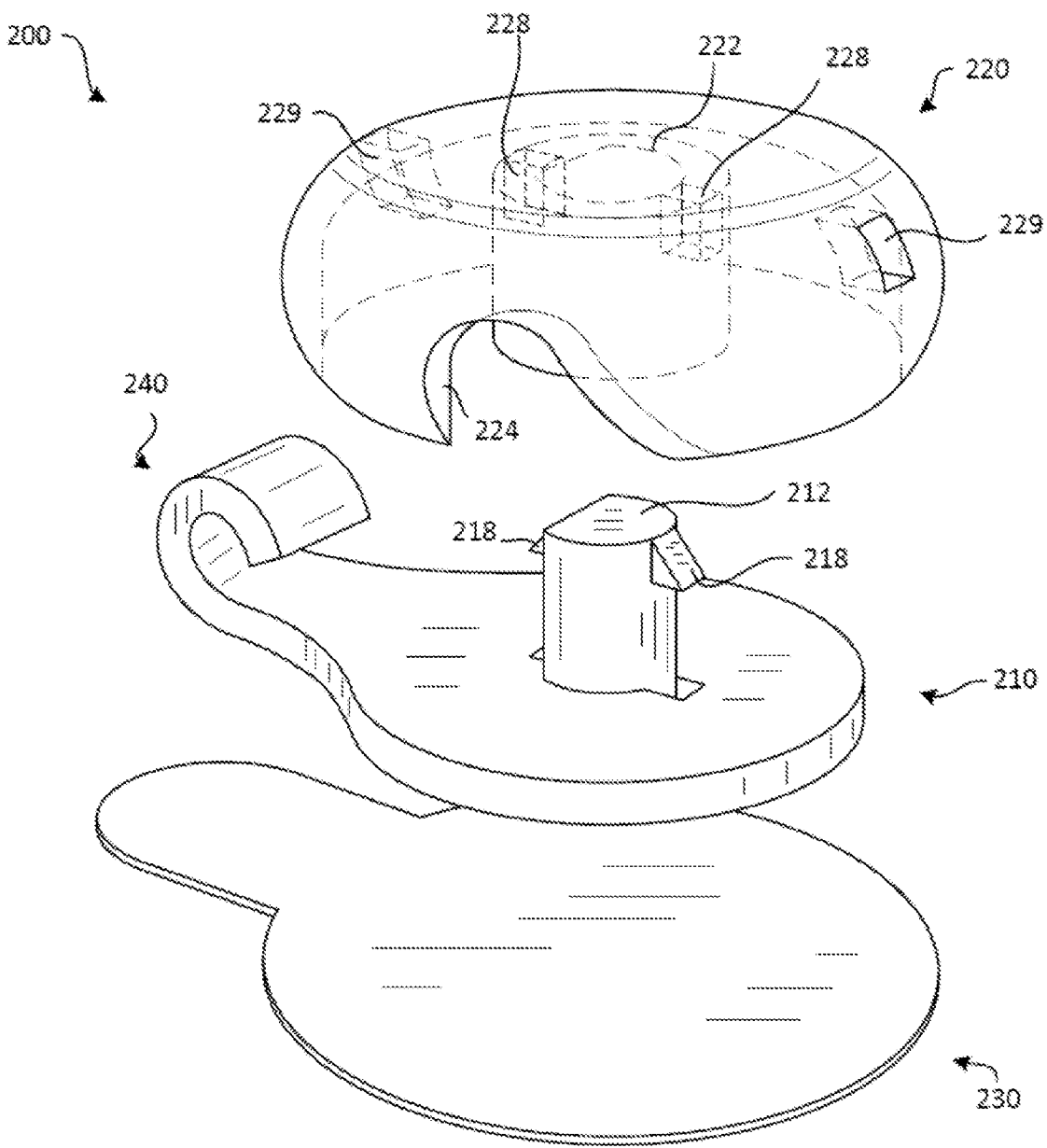
FIGS. 5A and 5B show various views of a securement assembly for securing the external portion of an access device or surgical drain, in accordance with various embodiments.
Figure 5B:
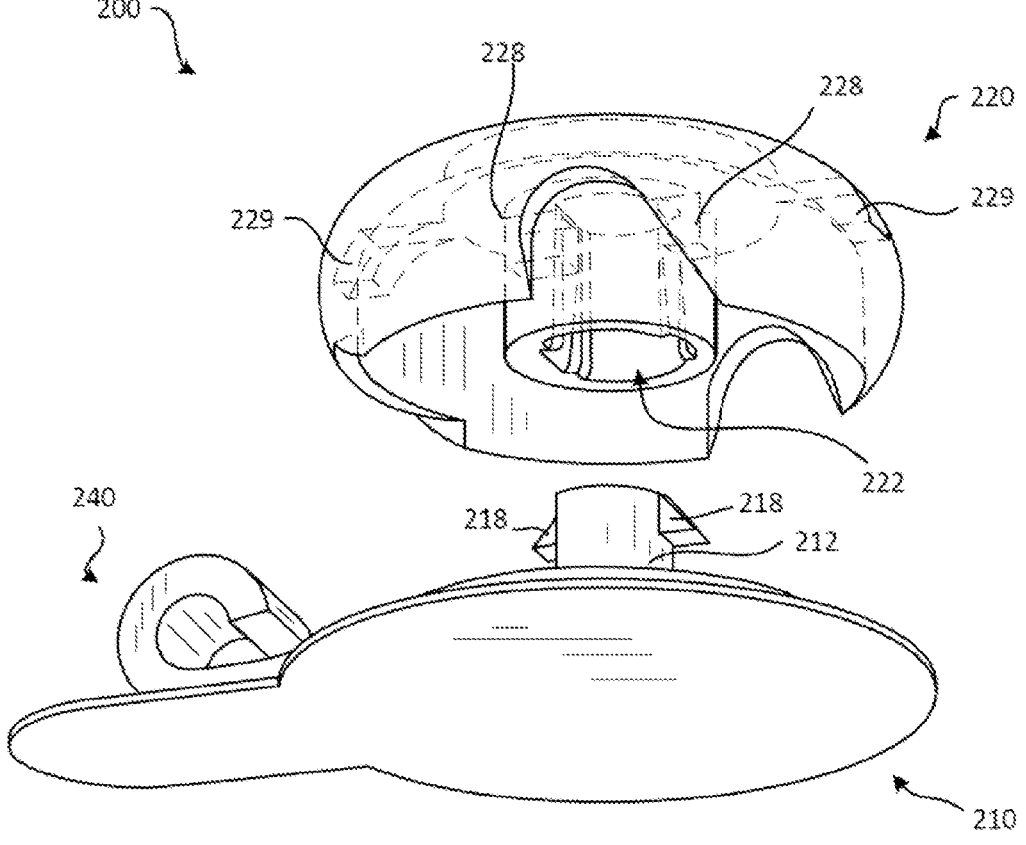

In various embodiments, and with reference to the accompanying figures, a securement assembly for an access device is provided. FIGS. 1A and 1B show details of a first implementation of the securement assembly 100, with FIGS. 2A, 2B, and 2C showing details of a second implementation of the securement assembly 200, in accordance with various embodiments. FIGS. 3A, 3B, 3C, and 3D show various steps of a method of installing/using the securement assembly to retain an external portion of an access device, according to various embodiments. FIGS. 4, 5A, and 5B generally show further features, components, and structures of the securement assembly, in accordance with various embodiments. Details and description herein pertaining to one of the figures is not necessarily limited to the referenced figure, and thus details pertaining to certain embodiments may also be implemented with other details from other embodiments.

In various embodiments, and with reference to FIGS. 1A and 1B, the securement assembly 100 for an access device 50 includes a base 110 and a lid 120. As mentioned above, the access device 50 may exit the body at an exit site, and an occlusion dressing may cover and protect the exit site. The portion of the access device that is outside of the skin of the patient is referred to as the external portion of the access device, and the securement assembly 100 is generally configured to secure and retain this external portion. Accordingly, the base 110 of the securement assembly 100 may have an adhesive layer 130 that facilitates attachment of the base 110 adjacent the exit sit (e.g., adjacent to the occlusion dressing). The base 110 may include a central post 112, and the external portion of the access device 50 may be configured to be wrapped around the central post 112.

Wrapping the external portion of the access device 50 (e.g., a catheter) around the central post 112 on the base 110 provides a stable, secure, and non-kinking method of reducing tension on the exit site and preventing accidental dislodgement of the catheter/access device. The securement assembly 100 may further include a clip extending from the base or the lid. For example, the clip 140 may extend from the base 110. Excess length of the access device may be retained by the clip in order to further prevent dislodgement that would otherwise be caused by the free/terminating end/port of the catheter dangling freely. The clip 140 may be designed to have a receptacle for the access device that is sized so as to be tight enough to hold the catheter in place, due to friction between the materials, but that still allows for the catheter to be slid by hand through the clip. In various embodiments, the clip may be specifically configured to secure a port of the external portion of the access device. Accordingly, the securement assembly 100, with its various components/structures 110, 120, 130, 140 that are described in greater detail below, generally provides improved practitioner usability by providing caregivers with a consistent and reliable securement method and provides an improved patient experience by increasing comfort and preventing device dislodgement, according to various embodiments.

In various embodiments, and with continued reference to FIGS. 1A and 1B, the base 110, which may be referred to as a housing, is generally configured to retain a section of the access device. The base may provide one, two, or three-dimensional stability by limiting displacement of the access device in one or more directions. In various embodiments, the central post 112 around which the catheter is to be wrapped is cylindrical. The central post 112 may be comprised of 4 quadrants, with each quadrant being capable of flexing inward to compress the post in response to tension on the access device (thereby inhibiting kinking or other damage to the access device). As used herein, the terms "inner" and "outer" refer to positions relative to the central post 112. That is, the central post 112 may be generally referred to as a center of the securement assembly 100 and may define a central post axis, and thus components or surfaces that are described as "inner" face toward or are disposed comparatively closer to the central post axis and components or surfaces that are described as "outer" face away from or are disposed comparatively farther from the central post axis.

In various embodiments, the base 110 and the lid 120 collectively define an annular chamber around the central post 112. The central post 112 may also have an upper lip to further facilitate secure retention of the access device in the annular chamber, and together with the lid 120 this upper lip prevents inadvertent upward movement of the access device once it has been inserted/installed around the central post 112. The diameter of the central post 112 may be such that fluid flow through the catheter wrapped around the central post 112 is not inhibited. The catheter may be wrapped fully around the post, or may be wrapped partially around the post. Further, the catheter may be wrapped in different directions around the post, depending on how long the external portion of the line is, and depending on the size of the annular chamber. In various embodiments, the securement assembly 100 is configured for a specific catheter size, or the securement assembly 100 may be configured to work with catheters of various sizes. In various embodiments, the overall size of the securement assembly is about 30 mm×30 mm×11 mm.

In various embodiments, the lid 120 of the securement assembly 100 extends from the base 110 and covers the external portion of the vascular access device. The lid may be detachably coupled to the base, hingedly coupled to the base, or the lid and the base may be made from a monolithic material such that a connecting portion (e.g., a neck) extending between the lid and the base forms a living hinge between the two components. In various embodiments, the lid 120 is configured to have a snap/interference fit with the base 110 (or at least corresponding features of the lid 120 and the base 110 are configured to detachably couple together). The lid 120 may further include one or more tabs or other features to facilitate a practitioner's ability to grasp the lid 120. The tabs may be offset from the center of the device, thereby enabling a peeling action to detach the lid from the base and thus preventing inadvertent lifting of the housed/wrapped access device.

In various embodiments, the lid 120 functions as a physical barrier/shield to prevent articles or objects from contacting the external portion of the access device wrapped around the central post and generally housed by the securement assembly. Thus, the lid 120 may facilitate retention of the access device within the annular chamber. The lid may have a smooth external, upper, and/or outer surface to prevent objects from catching on the securement assembly. That is, the lid may be substantially smooth and continuous (e.g., may be free of abrupt corners or interfaces).

In various embodiments, the base or the lid (or both) have a rim that forms an outer sidewall of the annular chamber. That is, the base and/or the lid may have a rim that forms a radially outward chamber wall to prevent the access device from unraveling/unwrapping. In various embodiments, and as described in greater detail below, the rim may have one or more windows or openings (e.g., may be a crenelated rim), and these windows or openings may facilitate insertion of the external portion of the access device into the annular chamber and/or may allow a practitioner to visibly inspect the wrapped access device.

The base and the lid may be rigid or semi-rigid. Accordingly, the securement assembly may be made from plastic, composite, or polymeric materials. For example, the base and/or lid may include acrylonitrile butadiene styrene (ABS), nylon, a co-polymer, thermoplastic or other polymer, polycarbonate, Silastic (silicone) or the like. The material selected may be capable of being sterilized, for example by ethylene oxide (EtO2). In various embodiments, and as described in greater detail below, sections and/or portions of the base and the lid may be resiliently flexible/deformable and may be made from other materials that are biodegradable. In various embodiments, the base may be more rigid than the lid. In various embodiments, the lid is made from a transparent material to allow inspection of the housed/wrapped catheter. The securement assembly may be made via a multi jet fusion 3D printing process or a steriolithography (SLA) 3D printing process or injection molded process. The base may have a shore hardness around 71 A, and the lid may be made of an elastomeric material with a shore hardness around 50 A. The materials have been chosen for this design due to their ease of manufacturability as well as the softness desired by the caretakers and patients. The flexibility of the lid allows for the catheter to be wrapped and covered easily without needing a snap fit lid that has the potential to pinch the line.

As mentioned above, the base 110 may be coupled to (or integrated with) an adhesive layer 130. The outer perimeter of the base 110 may be smaller than the outer perimeter of adhesive layer 130. In various embodiments, the shape and size of the base 110 and adhesive layer 130 may be customized for a specific use or to a specific age group of patients. The adherence provided by the adhesive layer 130 may be temporary (e.g., minutes, hours, or days) or semi-permanent (e.g., days, weeks, or months). In various embodiments, the adhesive layer 130 may be easily and atraumatically removable, so as to not cause pain or a significant skin rash or other irritation to the patient upon removal. Tape may be used in place of the adhesive layer to affix the base 110 to the skin surface of the patient. The adhesive layer may be comprised of a fabric or polymeric film with an adhesive bottom. Suitable materials for the adhesive layer 130 include, but are not limited to silicone or silicone-free adhesives with non-woven, woven, acrylic, or polyurethane backings that are biocompatible. In various embodiments, the upper surface of adhesive layer 130 does not comprise any backing, but rather, comprises an adhesive (e.g., acrylic) to attach to the base 110.

In various embodiments, and with reference to FIGS. 2A, 2B, and 2C, additional details are provided that may be implemented in conjunction with one or more of the details from the embodiment described above with reference to FIGS. 1A and 1B. In various embodiments, the securement assembly 200 includes a base 210 and a lid 220. The assembly 200 may further include an adhesive layer 230 and a clip 240. In various embodiments, the lid 220 is coupled to the base 210 via the central post 212. That is, the lid 220 may include an engagement feature that corresponds with an associated feature/shape of the central post 212 to enable a secure coupling between the lid and the base. In various embodiments, the base and the lid are permanently coupled together, or may be integrally formed together (e.g., may form a monolithic structure). The central post 212 may have a D-shaped cross-section, and the flat side of the post may interface with a corresponding flat section of a complementary receptacle 222 of the lid to ensure proper alignment between the lid and the base. That is, the lid may have a cylindrical socket with a D-shaped cavity that connects to the base portion.

In various embodiments, the lid 220 may be resiliently flexible (e.g., made from an elastomeric material) to allow its radially outward edges to be flexed outward and upward to allow insertion of the catheter into the annular chamber to be wrapped around the central post. In various embodiments, the lid 220 can be flipped up (e.g., similar to an inverted umbrella) so that the catheter can be wrapped underneath. In various embodiments, the resilient flexibility of the lid 220 allows for the catheter to be pushed underneath the lid from the side. As mentioned above, the rim of the lid 220 may have openings/windows 224 to allow for a practitioner to insert and/or withdraw the catheter from the annular chamber. The openings 224 are designed so that the rigidity of the parabolic lid shape is not compromised, according to various embodiments. For example, the catheter line may be inserted in a first opening, wound 360+ degrees around the center post, and exit out of a second opening. The openings 224 may be also slightly offset from the center of the lid to account for the natural way the line will enter and exit under the lid, tangent to the post when wrapped around it, according to various embodiments.

In various embodiments, and with specific reference to FIG. 2C, the lid 220 may also have a small notch 226 at the edge of the dome to allow for the lid to fit flush with the base, despite the extruded clip on a side of the base. That is, the lid 220 may define a notch 226 to accommodate an extension section of a clip 240 that extends from the base 210 of the securement assembly 200. In various embodiments, the rounded shape of the lid aims to reduce the possibility of catching on the patient's surroundings and to be comfortable, even when the patient is sleeping or exercising.

Figures 3A, 3B, 3C, 3D:
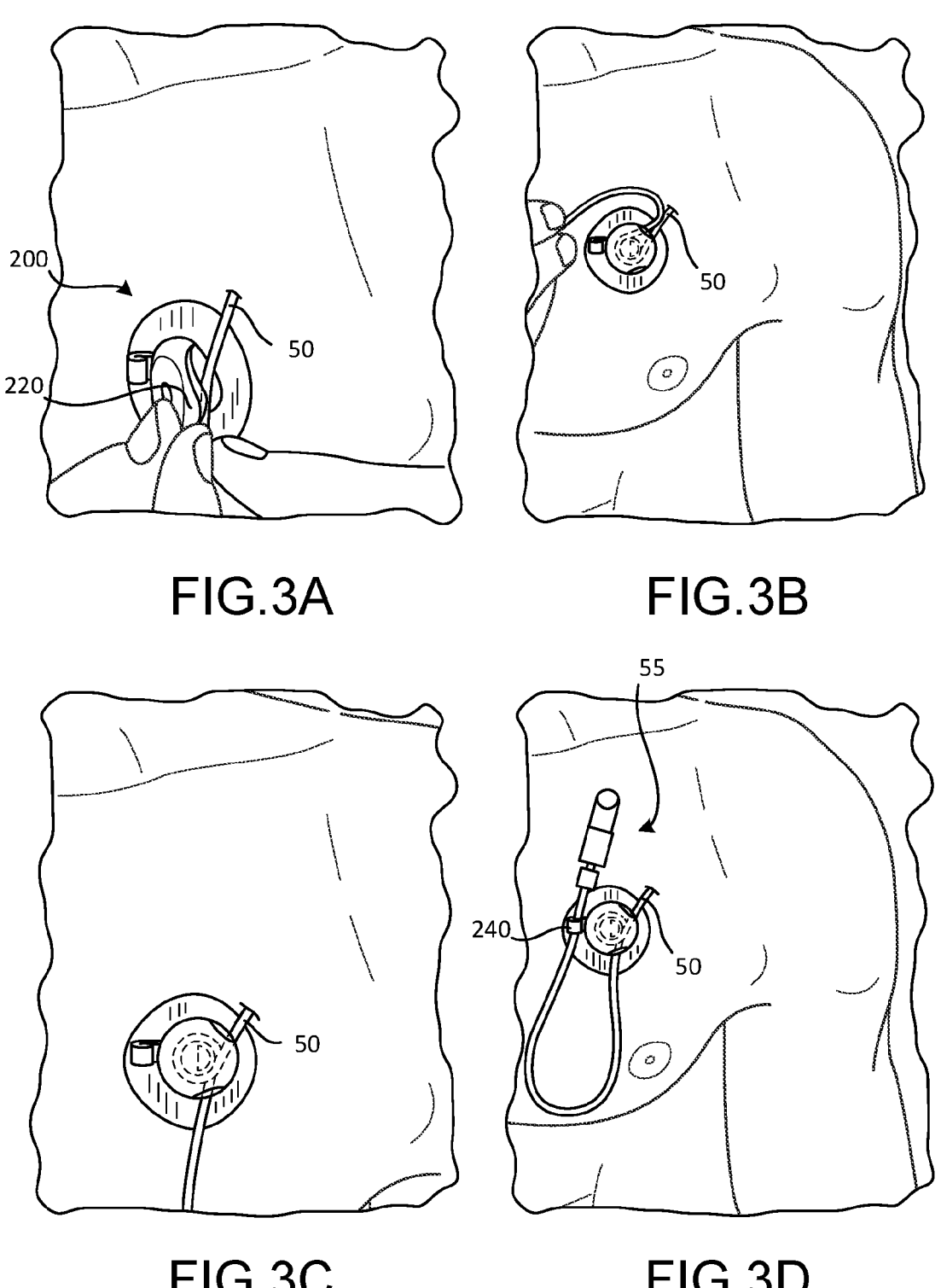
FIGS. 3A, 3B, 3C, and 3D show various views that show the steps of a method of securing the external portion of an access device or surgical drain, in accordance with various embodiments.

In various embodiments, and with reference to FIGS. 3A, 3B, 3C, and 3D, a method of securing the external portion of an access device or surgical drain is provided. The method may include locating where the catheter exits the occlusion dressing and cleaning the skin around it. The method may further include attaching the securement assembly to the skin adjacent the occlusion dressing (FIG. 3A). This step may include removing the adhesive backing from the base. The method may include lifting the rim of the lid (FIG. 3A) to insert the catheter or drain and then winding/wrapping the catheter or drain around the central post and closing the lid over the wrapped catheter or drain (FIG. 3B). The method may include wrapping the catheter or drain 360 degrees (or more) around the central post (FIG. 3C). In various embodiments, the lid may remain in a substantially closed/downward position as the catheter is wrapped around the central post. That is, the shape, material, and/or structure of the lid may be configured to allow the catheter to be received within the annular channel defined between the lid and the post in response to a wrapping, tension force applied to the catheter or drain. The method may further include further winding/wrapping excess length of the catheter or drain around the outer surfaces of the device and/or retaining the terminating end portion of the catheter or the suction bulb of a surgical into a clip (FIG. 3D).

In various embodiments, and with reference to FIG. 4, the securement assembly 200 may include multiple clips 240A, 240B for holding, retaining, and/or securing various sections of the external portion of the access device or surgical drain. For example, the securement assembly may have two clips, three clips, or more than three clips. In various embodiments, the clips 240A, 240B may be sized and configured to retain a specific type of catheter or port. The clips 240A, 240B may have a C-shape, and thus the clips may initially extend from the base region 210 of the assembly and may bend around more than 180 degrees to define a receptacle/socket for receiving the external portion of the access device or surgical drain. As used herein, reference to a bend angle or the extent of bending of the clip refers to curvature of the material that forms the clip and the bending, curved configuration of the extension direction of the clip. In various embodiments, the clip(s) bends about 235 degrees. In various embodiments, the clip(s) bend more than 235 degrees. In various embodiments, the clip bends about 270 degrees. As used in this context only, the term "about" refers to plus or minus 5% of the indicated value. In such embodiments, a gap is defined between the terminating end 242 of the bent clip and the base extension 243 of the clip. In various embodiments, and with continued reference to FIG. 4, the clip(s) 240A, 240B may have a finger tab 244 or a finger hold extending from a top surface thereof. The finger tab 244 may enable a user/practitioner to exert a force on the clip to force the terminating end 242 of the clip upwards and/or outwards (e.g., away from the base extension) 243 to facilitate insertion/retention of a catheter or port of the access device, or the suction bulb of a surgical drain. In various embodiments, the clip may be configured to retain the hub of a port 55 (e.g., see FIG. 2B) of a catheter, and thus the finger tabs 244 may allow for the catheter to be initially inserted into the clip, and then subsequent pulling/tension on the catheter may pull the catheter through the receptacle of the clip until the hub of the port (e.g., a venous hub) is engaged (e.g., via an interference fit) within the clip.

In various embodiments, and with reference to FIGS. 5A, and 5B, the central post 212 of the base 210 may have one or more protrusions 218 (e.g., tabs, flange sections, bosses, etc.) that are configured to be received by corresponding/complementary recesses 228 defined in the walls that define the post receptacle 222 of the lid 220. Said differently, the central post 212 of the base 210 may have one or more projections/protrusions 218 that extend from adjacent the distal/terminating end of the post and are configured to be received into corresponding recesses 228 to securely retain the lid 220 to the base 210, thereby preventing the lid 220 from being inadvertently decoupled from the base 210 and thereby mitigating chocking hazards (e.g., to promote a childproof connection). In various embodiments, the top surfaces of the protrusions 228 may be angled or curved to facilitate insertion through/into the main post receptacle 222 of the lid, but may have a flat underside that may be substantially perpendicular to the post 212 to inhibit the protrusions from becoming dislodged from the recesses 228. In various embodiments, the radially inward surface of the central post receptacle 222 may have channels and/or grooves to facilitate insertion of the central post 212 with protrusions 218 (e.g., to guide the mating interlock of the two pieces). In various embodiments, the exterior surface of the lid 220 may have corresponding openings 229 that accommodate a sliding cam or other such feature for forming the recesses 228 during the manufacturing/molding process.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. The benefits, advantages, solutions to problems, and any elements that may cause any benefit, advantage, or solution to occur or become more pronounced are not, however, to be construed as critical, required, or essential features or elements of the disclosure.

The scope of the disclosure is accordingly to be limited by nothing other than the appended claims, in which reference to an element in the singular is not intended to mean "one and only one" unless explicitly so stated, but rather "one or more." It is to be understood that unless specifically stated otherwise, references to "a," "an," and/or "the" may include one or more than one and that reference to an item in the singular may also include the item in the plural. All ranges and ratio limits disclosed herein may be combined.

Moreover, where a phrase similar to "at least one of A, B, and C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

Also, any reference to attached, fixed, connected, coupled or the like may include permanent (e.g., integral), removable, temporary, partial, full, and/or any other possible attachment option. Different cross-hatching is used throughout the figures to denote different parts but not necessarily to denote the same or different materials.

The steps recited in any of the method or process descriptions may be executed in any order and are not necessarily limited to the order presented. Furthermore, any reference to singular includes plural embodiments, and any reference to more than one component or step may include a singular embodiment or step. Elements and steps in the figures are illustrated for simplicity and clarity and have not necessarily been rendered according to any particular sequence. For example, steps that may be performed concurrently or in different order are illustrated in the figures to help to improve understanding of embodiments of the present disclosure.

Any reference to attached, fixed, connected or the like may include permanent, removable, temporary, partial, full and/or any other possible attachment option. Additionally, any reference to without contact (or similar phrases) may also include reduced contact or minimal contact. Surface shading lines may be used throughout the figures to denote different parts or areas but not necessarily to denote the same or different materials. In some cases, reference coordinates may be specific to each figure.

Systems, methods and apparatus are provided herein. In the detailed description herein, references to "one embodiment", "an embodiment", "various embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A securement assembly for an access device or surgical drain ("access device"), the securement assembly comprising:
    a base comprising a central post, wherein an external portion of the access device is configured to be wrapped around the central post; and
    a resiliently flexible and flippable lid extending from the base and configured to cover the external portion of the access device, the lid comprising radially outward edges to allow the wrapped access device underneath the lid.

2. The securement assembly of claim 1, wherein the base and the lid collectively define an annular chamber around the central post of the base.

3. The securement assembly of claim 2, wherein at least one of the base and the lid comprises a rim that forms an outer sidewall of the annular chamber.

4. The securement assembly of claim 3, wherein the rim defines one or more crenels thatfacilitate insertion of the external portion of the access device into the annular chamber.

5. The securement assembly of claim 1, further comprising an adhesive layer coupled to the base.

6. The securement assembly of claim 1, further comprising a clip extending from at least one of the base and the lid, wherein the clip is configured to detachably retain a port or reservoir of the external portion of the access device.

7. The securement assembly of claim 6, wherein the clip is a first clip, wherein the securement assembly further comprises a second clip extending from at least one of the base and the lid, wherein the second clip is also configured to detachably retain another port or reservoir of the external portion of the access device.

8. The securement assembly of claim 6, wherein the clip comprises a finger tab protruding from an upper surface of the clip.

9. The securement assembly of claim 6, wherein the clip extends from the base and bends around more than 180 degrees such that a terminating end of the clip is facing back toward the lid.

10. The securement assembly of claim 9, wherein the clip extends from the base and bends around about 235 degrees.

11. The securement assembly of claim 1, wherein the lid comprises a post receptacle configured to receive the central post of the base.

12. The securement assembly of claim 11, wherein the central post and the post receptacle have a D-shaped cross-section.

13. The securement assembly of claim 11, wherein the central post comprises a protrusion and a recess is defined in a wall of the post receptacle, wherein the recess is configured to receive the protrusion to couple the lid to the base.

14. The securement assembly of claim 13, wherein a radially inward surface of the wall of the post receptacle comprises a channel for receiving the protrusion during inserting of the central post into the post receptacle.

15. The securement assembly of claim 13, wherein the protrusion comprises an upper surface that is slanted and a lower surface that is perpendicular to the central post.

16. A securement assembly for an access device or surgical drain ("access device"), the securement assembly comprising:
    a base comprising a central post, wherein an external portion of the access device is configured to be wrapped around the central post;
    a lid extending from the base and configured to cover the external portion of the access device, the lid comprising radially outward edges to allow the wrapped access device underneath the lid; and
    a clip extending from the base;
    wherein the base and the lid collectively define an annular chamber around the central post of the base; and
    wherein the clip is configured to detachably retain at least one of a port and a catheter of the external portion of the access device.

17. The securement assembly of claim 16, wherein the lid comprises a post receptacle configured to receive the central post of the base.

18. The securement assembly of claim 17, wherein the central post and the post receptacle have a D-shaped cross-section.

19. The securement assembly of claim 17, wherein the central post comprises a protrusion and a recess is defined in a wall of the post receptacle, wherein the recess is configured to receive the protrusion to couple the lid to the base.

20. The securement assembly of claim 19, wherein the protrusion comprises an upper surface that is slanted and a lower surface that is perpendicular to the central post.

* * * * *